US008821521B2

(12) United States Patent
Burnett

(10) Patent No.: US 8,821,521 B2
(45) Date of Patent: Sep. 2, 2014

(54) GASTRO-INTESTINAL DEVICE AND METHOD FOR TREATING ADDICTION

(75) Inventor: Daniel R. Burnett, San Francisco, CA (US)

(73) Assignee: BAROnova, Inc., Goleta, CA (US)

(*) Notice: Subject to any disclaimer, the term of this patent is extended or adjusted under 35 U.S.C. 154(b) by 1500 days.

(21) Appl. No.: 11/702,888

(22) Filed: Feb. 5, 2007

(65) Prior Publication Data

US 2007/0178160 A1  Aug. 2, 2007

Related U.S. Application Data

(63) Continuation-in-part of application No. 10/915,716, filed on Aug. 9, 2004, which is a continuation-in-part (Continued)

(51) Int. Cl.
*A61K 9/14* (2006.01)
*A61F 5/00* (2006.01)

(Continued)

(52) U.S. Cl.
CPC ........... *A61F 5/0079* (2013.01); *A61N 1/06* (2013.01); *A61B 5/036* (2013.01); *A61B 5/14546* (2013.01); *A61B 5/4238* (2013.01); *A61B 17/12099* (2013.01); *A61B 2017/00876* (2013.01); *A61B 5/145* (2013.01); *A61F 2002/044* (2013.01); *A61B 17/12022* (2013.01); *A61B 17/12172* (2013.01); *A61B 17/12036* (2013.01); *A61B 2017/12086* (2013.01); *A61B 17/12136* (2013.01); *A61F 5/003* (2013.01); *A61B 5/073* (2013.01); *A61F 2/24* (2013.01); *A61N 1/40* (2013.01); *A61F 5/0036* (2013.01); *A61B 5/14539* (2013.01); *A61B 17/1219* (2013.01)
USPC ........................................ 606/151; 623/23.65

(58) Field of Classification Search
CPC ............... A61B 17/12022; A61B 17/12036; A61B 17/12099; A61F 5/003; A61F 5/0013; A61F 5/0036; A61F 5/0079
USPC ............... 606/151, 155, 153, 157; 623/23.65, 623/23.67, 23.69
See application file for complete search history.

(56) References Cited

U.S. PATENT DOCUMENTS

| 2,499,045 A | 2/1950 | Ray et al. |
| 4,133,315 A | 1/1979 | Berman et al. |

(Continued)

FOREIGN PATENT DOCUMENTS

| DE | 4012642 | 10/1991 |
| WO | WO 90/00369 | 1/1990 |

(Continued)

OTHER PUBLICATIONS

European Patent Application No. 04778818.7 filed Jul. 20, 2004 in the name of Burnett et al., Office Action mailed Oct. 5, 2009.

(Continued)

*Primary Examiner* — Julian W Woo
*Assistant Examiner* — Shaun L David
(74) *Attorney, Agent, or Firm* — Levine Bagade Han LLP

(57) ABSTRACT

A device and a method for treating a medical condition include a reversible member disposed in a patient's gastro-intestinal tract, and a dispensing member coupled to the reversible member that delivers a drug and/or a noxious when a predetermined substance is detected. In a different embodiment, the device and method of the present invention include a polymer infused with a drug and disposed into a preformed shell inside the gastric space, where it expands and hardens, releasing the drug over time. Both the casing and the polymer may be biocompatible. The present invention enables the slow-release of anti-addictive agents without patient tampering and with the appropriate dosage. Ancillary systems such as sensors, actuators, refill and recharge ports, and communication and data processing units may also be included.

22 Claims, 16 Drawing Sheets

(51) Int. Cl.
*A61B 5/145* (2006.01)
*A61B 5/00* (2006.01)
*A61B 17/12* (2006.01)
*A61N 1/06* (2006.01)
*A61B 5/03* (2006.01)
*A61B 17/00* (2006.01)
*A61F 2/04* (2013.01)
*A61B 5/07* (2006.01)
*A61F 2/24* (2006.01)
*A61N 1/40* (2006.01)

Related U.S. Application Data of application No. 10/833,950, filed on Apr. 27, 2004, and a continuation-in-part of application No. 10/671,191, filed on Sep. 24, 2003, now Pat. No. 6,994,095.

(60) Provisional application No. 60/525,105, filed on Nov. 26, 2003, provisional application No. 60/490,421, filed on Jul. 23, 2003, provisional application No. 60/764,673, filed on Feb. 3, 2006.

(56) References Cited

U.S. PATENT DOCUMENTS

| | | | |
|---|---|---|---|
| 4,240,412 A | 12/1980 | James | |
| 4,246,893 A | 1/1981 | Berson | |
| 4,315,509 A | 2/1982 | Smit | |
| 4,368,739 A | 1/1983 | Nelson | |
| 4,416,267 A | 11/1983 | Garren et al. | |
| 4,485,805 A | 12/1984 | Foster, Jr. | |
| 4,517,979 A | 5/1985 | Pecenka | |
| 4,657,020 A | 4/1987 | Lifton | |
| 4,694,827 A | 9/1987 | Weiner et al. | |
| 4,735,214 A | 4/1988 | Berman | |
| 4,762,128 A | 8/1988 | Rosenbluth | |
| 4,836,204 A | 6/1989 | Landymore et al. | |
| 4,878,905 A | 11/1989 | Blass | |
| 4,925,446 A * | 5/1990 | Garay et al. | 604/103.02 |
| 4,930,496 A | 6/1990 | Bosley | |
| 5,011,488 A | 4/1991 | Ginsburg | |
| 5,108,420 A | 4/1992 | Marks | |
| 5,129,915 A | 7/1992 | Cantenys | |
| 5,192,301 A | 3/1993 | Kamiya et al. | |
| 5,246,445 A | 9/1993 | Yachia et al. | |
| 5,282,829 A | 2/1994 | Hermes | |
| 5,306,300 A | 4/1994 | Berry | |
| 5,312,343 A | 5/1994 | Krog et al. | |
| 5,423,872 A | 6/1995 | Cigaina | |
| 5,509,888 A | 4/1996 | Miller | |
| 5,514,091 A | 5/1996 | Yoon | |
| 5,514,178 A | 5/1996 | Torchio | |
| 5,540,701 A | 7/1996 | Sharkey et al. | |
| 5,545,210 A | 8/1996 | Hess et al. | |
| 5,634,936 A | 6/1997 | Linden et al. | |
| 5,676,688 A | 10/1997 | Jaker et al. | |
| 5,750,585 A | 5/1998 | Park et al. | |
| 5,752,971 A | 5/1998 | Rosenbluth et al. | |
| 5,782,800 A | 7/1998 | Yoon | |
| 5,820,584 A | 10/1998 | Crabb | |
| 5,853,422 A | 12/1998 | Huebsch et al. | |
| 5,976,174 A | 11/1999 | Ruiz | |
| 6,067,991 A | 5/2000 | Forsell | |
| 6,102,928 A | 8/2000 | Bonutti | |
| 6,112,703 A | 9/2000 | Handelsman | |
| 6,117,159 A | 9/2000 | Huebsch et al. | |
| 6,152,144 A | 11/2000 | Lesh et al. | |
| 6,159,219 A | 12/2000 | Ren | |
| 6,162,201 A | 12/2000 | Cohen | |
| 6,183,520 B1 | 2/2001 | Pintauro et al. | |
| 6,245,090 B1 | 6/2001 | Gilson et al. | |
| 6,270,515 B1 | 8/2001 | Linden et al. | |
| 6,371,974 B1 | 4/2002 | Brenneman et al. | |
| 6,409,656 B1 | 6/2002 | Sangouard et al. | |
| 6,488,962 B1 | 12/2002 | Berner et al. | |
| 6,527,701 B1 | 3/2003 | Sayet et al. | |
| 6,527,739 B1 | 3/2003 | Bigus et al. | |
| 6,540,789 B1 | 4/2003 | Silverman et al. | |
| 6,544,291 B2 | 4/2003 | Taylor | |
| 6,558,400 B2 | 5/2003 | Deem et al. | |
| 6,579,301 B1 | 6/2003 | Bales et al. | |
| 6,600,953 B2 | 7/2003 | Flesler et al. | |
| 6,652,578 B2 | 11/2003 | Bailey et al. | |
| 6,675,809 B2 | 1/2004 | Stack et al. | |
| 6,689,046 B2 | 2/2004 | Sayet et al. | |
| 6,702,846 B2 | 3/2004 | Mikus | |
| 6,740,121 B2 | 5/2004 | Geitz | |
| 6,755,869 B2 | 6/2004 | Geitz | |
| 6,802,868 B2 | 10/2004 | Silverman et al. | |
| 6,994,095 B2 | 2/2006 | Burnett | |
| 7,011,621 B2 | 3/2006 | Sayet et al. | |
| 7,037,344 B2 | 5/2006 | Kagan et al. | |
| 7,054,690 B2 | 5/2006 | Imran et al. | |
| 7,087,072 B2 | 8/2006 | Marino et al. | |
| 7,120,498 B2 | 10/2006 | Imran et al. | |
| 7,121,283 B2 | 10/2006 | Stack et al. | |
| 7,122,058 B2 | 10/2006 | Levine et al. | |
| 7,146,984 B2 | 12/2006 | Stack et al. | |
| 7,160,312 B2 | 1/2007 | Saadat | |
| 7,167,750 B2 | 1/2007 | Knudson et al. | |
| 7,842,053 B2 | 11/2010 | Chanduszko et al. | |
| 8,048,169 B2 | 11/2011 | Burnett et al. | |
| 2002/0013601 A1 | 1/2002 | Nobles et al. | |
| 2002/0038100 A1 | 3/2002 | Okada | |
| 2002/0091395 A1 | 7/2002 | Gabbay | |
| 2002/0165589 A1 | 11/2002 | Imran et al. | |
| 2002/0188354 A1 | 12/2002 | Peghini | |
| 2002/0198470 A1 | 12/2002 | Imran et al. | |
| 2003/0023150 A1 | 1/2003 | Yokoi et al. | |
| 2003/0040804 A1 | 2/2003 | Stack et al. | |
| 2003/0078611 A1 | 4/2003 | Hashiba et al. | |
| 2003/0093117 A1 | 5/2003 | Saadat | |
| 2003/0109931 A1 | 6/2003 | Geitz | |
| 2003/0109935 A1 | 6/2003 | Geitz | |
| 2003/0120328 A1 | 6/2003 | Jenkins et al. | |
| 2003/0144708 A1 | 7/2003 | Starkebaum | |
| 2003/0152601 A1 | 8/2003 | Kanayama | |
| 2003/0153806 A1 | 8/2003 | Miller | |
| 2003/0158601 A1 | 8/2003 | Silverman et al. | |
| 2004/0034408 A1 | 2/2004 | Majercack | |
| 2004/0107004 A1 | 6/2004 | Levine et al. | |
| 2004/0117031 A1 | 6/2004 | Stack et al. | |
| 2004/0158331 A1 | 8/2004 | Stack et al. | |
| 2004/0172141 A1 | 9/2004 | Stack et al. | |
| 2004/0172142 A1 | 9/2004 | Stack et al. | |
| 2004/0230222 A1 | 11/2004 | van der Burg et al. | |
| 2004/0236357 A1 | 11/2004 | Kraemer et al. | |
| 2004/0267378 A1 | 12/2004 | Gazi et al. | |
| 2005/0033331 A1 | 2/2005 | Burnett et al. | |
| 2005/0033332 A1 | 2/2005 | Burnett | |
| 2005/0038460 A1 | 2/2005 | Jayaraman | |
| 2005/0055039 A1 | 3/2005 | Burnett | |
| 2005/0090873 A1 | 4/2005 | Imran et al. | |
| 2005/0096673 A1 | 5/2005 | Stack et al. | |
| 2005/0149142 A1 * | 7/2005 | Starkebaum | 607/40 |
| 2005/0192629 A1 | 9/2005 | Saadat et al. | |
| 2005/0273060 A1 | 12/2005 | Levy et al. | |
| 2006/0020278 A1 | 1/2006 | Burnett et al. | |
| 2006/0178691 A1 | 8/2006 | Binmoeller | |
| 2006/0217763 A1 | 9/2006 | Abbott et al. | |
| 2006/0282107 A1 | 12/2006 | Hashiba et al. | |
| 2006/0293742 A1 | 12/2006 | Dann et al. | |
| 2007/0016262 A1 | 1/2007 | Gross et al. | |
| 2007/0027548 A1 | 2/2007 | Levine et al. | |
| 2007/0056591 A1 | 3/2007 | McSwain | |
| 2007/0083224 A1 | 4/2007 | Hively | |
| 2007/0135831 A1 | 6/2007 | Burnett et al. | |
| 2007/0198082 A1 | 8/2007 | Kapadia et al. | |
| 2007/0239284 A1 * | 10/2007 | Skerven et al. | 623/23.65 |
| 2007/0250132 A1 | 10/2007 | Burnett | |
| 2009/0118757 A1 | 5/2009 | Burnett et al. | |
| 2009/0118758 A1 | 5/2009 | Burnett et al. | |

(56) References Cited

U.S. PATENT DOCUMENTS

| | | |
|---|---|---|
| 2009/0177288 A1 | 7/2009 | Wallsten |
| 2009/0182357 A1 | 7/2009 | Burnett et al. |
| 2009/0182358 A1 | 7/2009 | Burnett et al. |
| 2009/0187200 A1 | 7/2009 | Burnett et al. |
| 2009/0187201 A1 | 7/2009 | Burnett et al. |
| 2009/0198210 A1 | 8/2009 | Burnett et al. |
| 2009/0216262 A1 | 8/2009 | Burnett et al. |

FOREIGN PATENT DOCUMENTS

| | | |
|---|---|---|
| WO | WO 00/48672 | 8/2000 |
| WO | WO 02/091961 | 11/2002 |
| WO | WO 03/017882 | 3/2003 |
| WO | WO 2005/009288 | 2/2005 |
| WO | WO 2005/104989 | 10/2005 |
| WO | WO 2006/020370 | 2/2006 |
| WO | WO 2006/135857 | 12/2006 |
| WO | WO 2007/027812 | 3/2007 |
| WO | WO 2007/092390 | 8/2007 |
| WO | WO 2007/092501 | 8/2007 |
| WO | WO 2009/033049 | 3/2009 |

OTHER PUBLICATIONS

U.S. Appl. No. 10/915,716, filed Aug. 9, 2004 in the name of Burnett et al., Non-final Office Action mailed Dec. 8, 2009.
European Patent Application No. 05774631.5 filed Jul. 25, 2005 in the name of Burnett et al., Supplementary Partial European Search Report and Opinion mailed Dec. 1, 2009.
European Patent Application No. 05774631.5 filed Jul. 25, 2005 in the name of Burnett et al., Office Action mailed Mar. 16, 2010.
Canadian Patent Application No. 2,534,118 filed Jul. 20, 2004 in the name of Burnett et al., Office Action mailed Apr. 1, 2010.
European Patent Application No. 07763667.8 filed Feb. 5, 2007 in the name of Burnett, Search Report and Opinion mailed Dec. 23, 2009.
European Patent Application No. 07763667.8 filed Feb. 5, 2007 in the name of Burnett, Office Action mailed Apr. 12, 2010.
U.S. Appl. No. 11/702,840, filed Feb. 5, 2007 in the name of Burnett et al., non-final Office Action mailed Feb. 4, 2010.
U.S. Appl. No. 10/833,950, filed Apr. 27, 2004 in the name of Burnett et al., final Office Action mailed Jan. 28, 2010.
Canadian Patent Application No. 2,620,859 filed Aug. 29, 2006 in the name of Burnett at al., Office Action mailed Apr. 20, 2010.
U.S. Appl. No. 12/351,686, filed Jan. 9, 2009 in the name of Burnett et al., non-final Office Action mailed Jul. 8, 2010.
Australian Patent Application No. 2004258968 filed Jul. 20, 2004 in the name of Baranova, Inc. Office Action mailed Feb. 10, 2011.
Australian Patent Application No. 2004258968 filed Jul. 20, 2004 in the name of Baranova, Inc., Office Action mailed Jan. 11, 2010.
Australian Patent Application No. 2005274132 filed Jul. 25, 2005 in the name of Baranova, Inc., Office Action mailed Mar. 22, 2010.
Australian Patent Application No. 2006284801 filed Aug. 29, 2006 in the name of Baranova, Inc., Office Action mailed Oct. 16, 2009.
Canadian Patent Application No. 2,534,118 filed Jul. 20, 2004 in the name of Baranova, Inc., Notice of Allowance mailed Jan. 24, 2011.
Canadian Patent Application No. 2,576,476 filed Jul. 25, 2005 in the name of Baranova, Inc., Office Action mailed Dec. 3, 2010.
Canadian Patent Application No. 2,620,859 filed Aug. 29, 2006 in the name of Baranova, Inc., Notice of Allowance mailed Feb. 4, 2011.
Japanese Patent Application No. 2006-521910 filed Jul. 20, 2004 in the name of Polymorfix, Inc., Office Action mailed Mar. 9, 2010.
U.S. Appl. No. 10/833,950, filed Apr. 27, 2004 in the name of Burnett et al., Non-final Office Action mailed Nov. 17, 2010.
U.S. Appl. No. 10/915,716, filed Aug. 9, 2004 in the name of Burnett et al., Final Office Action mailed Dec. 29, 2010.
U.S. Appl. No. 11/702,840, filed Feb. 5, 2007 in the name of Burnett, Final Office Action mailed Oct. 27, 2010.
U.S. Appl. No. 12/351,686, filed Jan. 9, 2009 in the name of Burnett et al., final Office Action mailed Mar. 11, 2011.
U.S. Appl. No. 12/351,705, filed Jan. 9, 2009 in the name of Burnett et al., Non-final Office Action mailed Sep. 29, 2010.
U.S. Appl. No. 12/352,497 filed Jan. 12, 2009 in the name of Burnett et al., Non-final Office Action mailed Dec. 23, 2010.
U.S. Appl. No. 11/215,430, filed Aug. 29, 2005 in the name of Burnett et al., Non-final Office Action mailed Mar. 23, 2011.
U.S. Appl. No. 12/434,594, filed May 1, 2009 in the name of Burnett et al., Non-final Office Action mailed Mar. 24, 2011.
U.S. Appl. No. 12/351,644, filed Jan. 9, 2009 in the name of Burnett et al., Non-final Office Action mailed Mar. 24, 2011.
U.S. Appl. No. 12/351,665, filed Jan. 9, 2009 in the name of Burnett et al., Non-final Office Action mailed Mar. 24, 2011.
U.S. Appl. No. 11/602,620, filed Nov. 20, 2006 in the name of Burnett, Non-final Office Action mailed Mar. 29, 2011.
U.S. Appl. No. 10/671,191, filed Sep. 24, 2003 in the name of Burnett, Non-final Office Action mailed Dec. 15, 2004.
U.S. Appl. No. 10/671,191, filed Sep. 24, 2003 in the name of Burnett, Notice of Allowance mailed Sep. 13, 2005.
U.S. Appl. No. 10/833,950, filed Apr. 27, 2004 in the name of Burnett et al., Non-final Office Action mailed Apr. 15, 2009.
U.S. Appl. No. 10/915,716, filed Aug. 9, 2004 in the name of Burnett et al., Final Office Action mailed Mar. 19, 2009.
U.S. Appl. No. 10/915,716, filed Aug. 9, 2004 in the name of Burnett et al., Non-final Office Action mailed May 29, 2008.
U.S. Appl. No. 11/215,430, filed Aug. 29, 2005 in the name of Burnett et al., Final Office Action mailed May 28, 2008.
U.S. Appl. No. 11/215,430, filed Aug. 29, 2005 in the name of Burnett et al., Non-final Office Action mailed Feb. 13, 2009.
U.S. Appl. No. 11/215,430, filed Aug. 29, 2005 in the name of Burnett et al., Non-final Office Action mailed Mar. 8, 2007.
International Patent Application No. PCT/US2005/026370 filed Jul. 25, 2005 in the name of Baronova, Inc., International Search Report and Written Opinion mailed Sep. 30, 2008.
International Patent Application No. PCT/US2007/003052 filed Feb. 5, 2007 in the name of Baronova, Inc., International Search Report and Written Opinion mailed Nov. 19, 2007.
International Patent Application No. PCT/US2007/003260 filed Feb. 5, 2007 in the name of Baronova, Inc., International Search Report and Written Opinion mailed Sep. 26, 2008.
International Patent Application No. PCT/US2008/075439 filed Sep. 5, 2008 in the name of Baronova, Inc., International Search Report and Written Opinion mailed Nov. 10, 2008.
International Patent Application No. PCT/US2006/033923 filed Aug. 29, 2006 in the name of Baronova, Inc., International Search Report and Written Opinion mailed Jan. 18, 2008.
International Patent Application No. PCT/US2004/023470 filed Jul. 20, 2004 in the name of Polymorfix, Inc., International Search Report and Written Opinion mailed May 27, 2005.
U.S. Appl. No. 10/671,191, filed Sep. 24, 2003 in the name of Burnett, Final Office Action mailed May 5, 2005.
U.S. Appl. No. 11/702,840, Daniel R. Burnett.
Australian Patent Application No. 2007212404 filed Feb. 5, 2007 in the name of Baranova, Inc., Office Action mailed May 2, 2011.
U.S. Appl. No. 11/702,840, filed Feb. 5, 2007 in the name of Burnett et al., Non-final Office Action mailed May 20, 2011.
U.S. Appl. No. 12/351,705, filed Jan. 9, 2009 in the name of Burnett et al., final Office Action mailed Jun. 9, 2011.
Japanese Patent Application No. 2007-525638 filed Jul. 25, 2005 in the name of Baranova, Inc., Office Action mailed Jan. 4, 2011.
European Patent Application No. 05774631.5 filed Jul. 25, 2005 in the name of Baranova, Inc., Office Action mailed Mar. 25, 2011.
Japanese Patent Application No. 2008-529243 filed Aug. 29, 2006 in the name of Baranova, Inc., Office Action mailed May 17, 2011.
Australian Patent Application No. 2007212473 filed Feb. 5, 2007 in the name of Baranova, Inc., Office Action mailed Apr. 20, 2011.

* cited by examiner

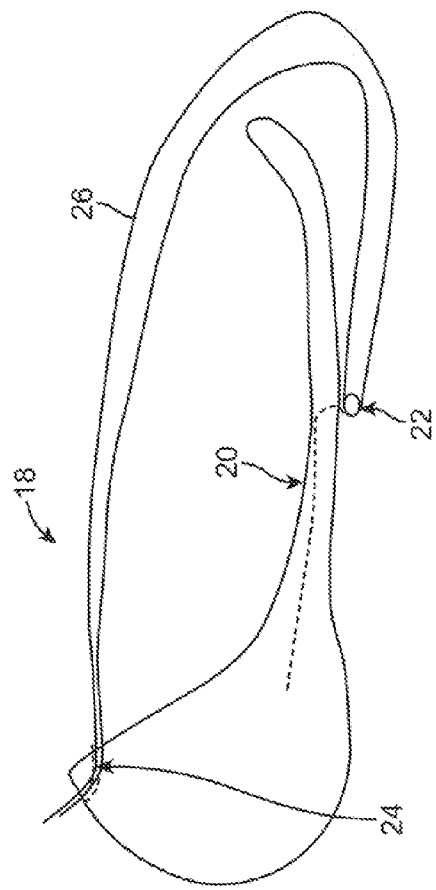
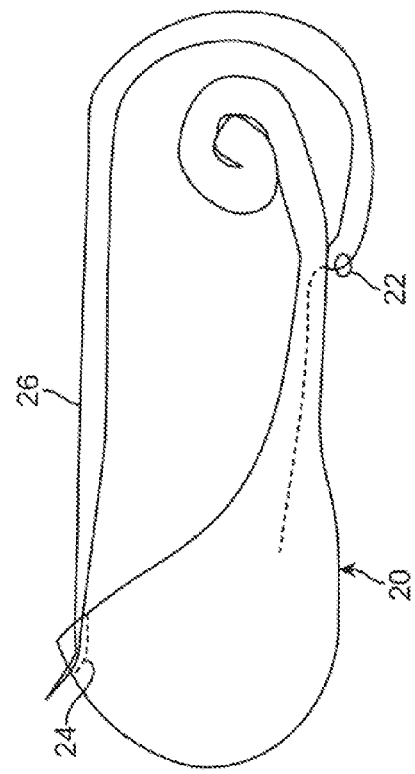
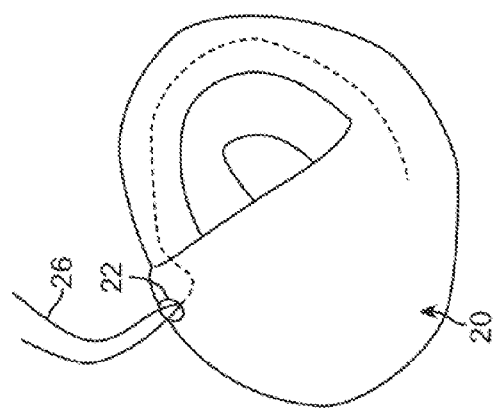

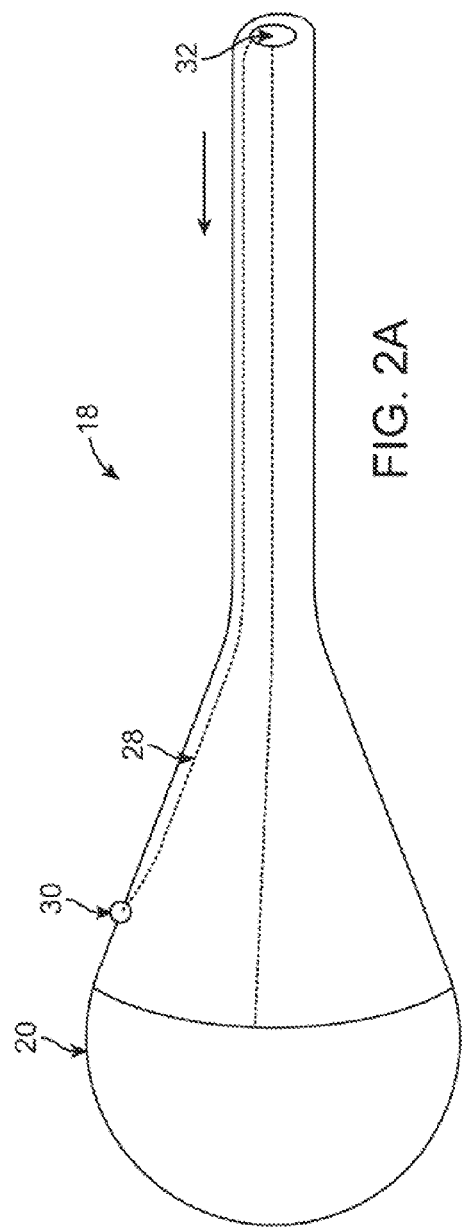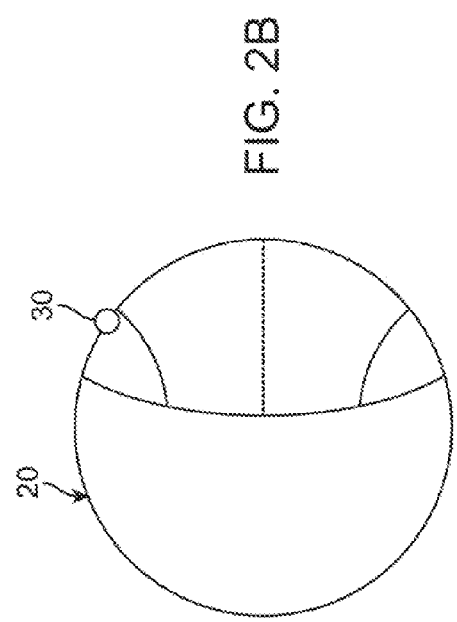

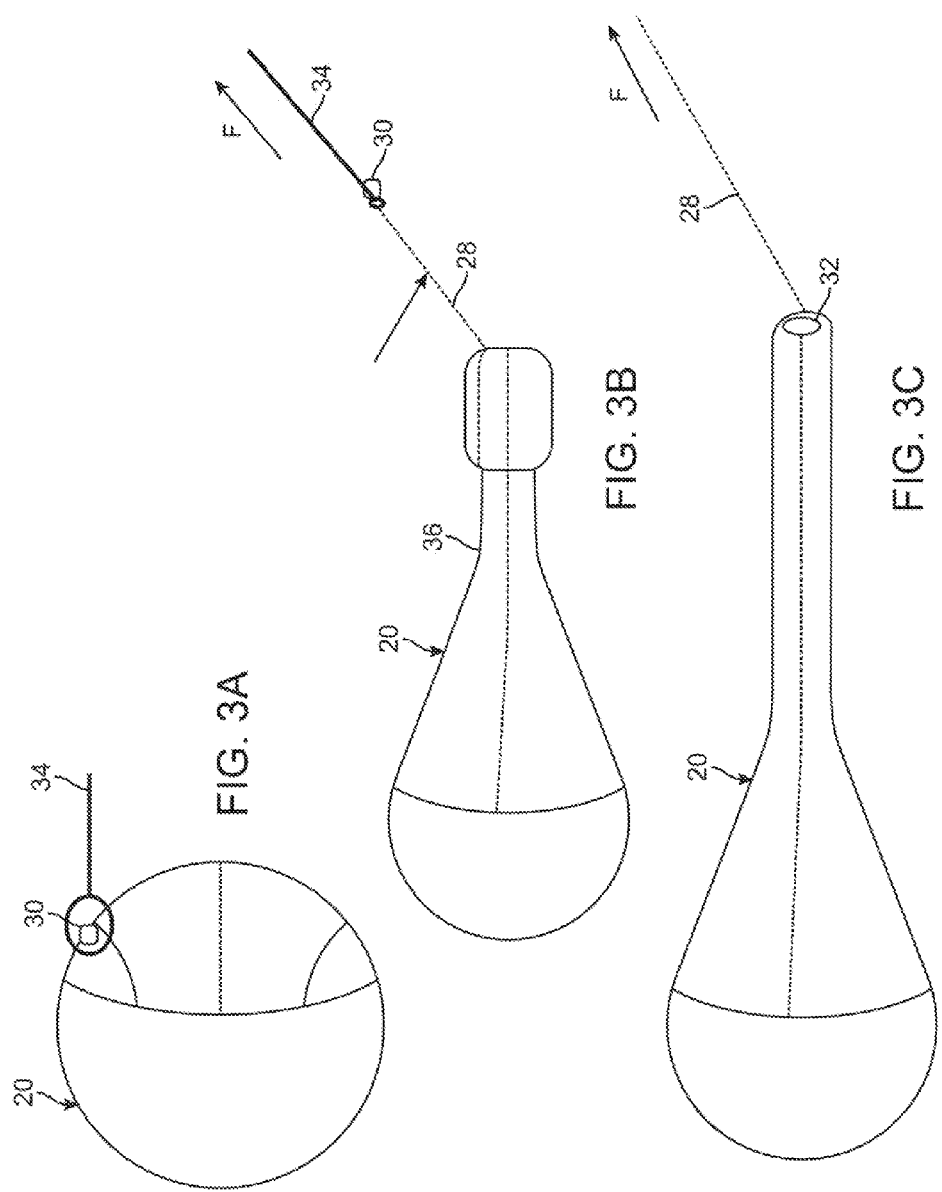

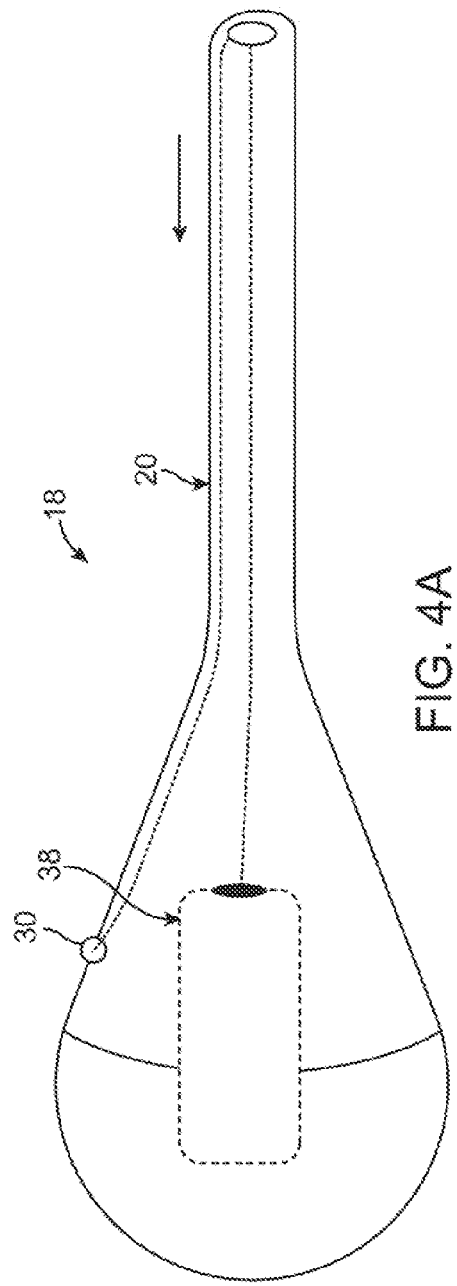
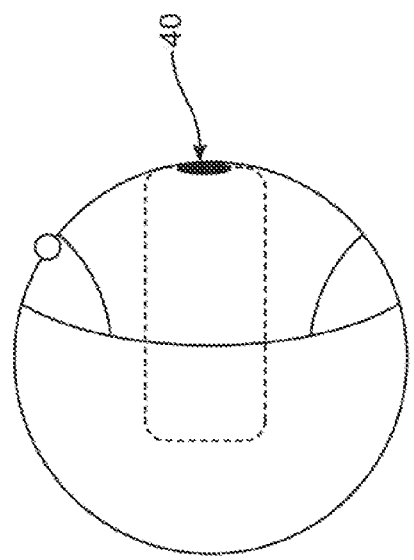
FIG. 4A
FIG. 4B

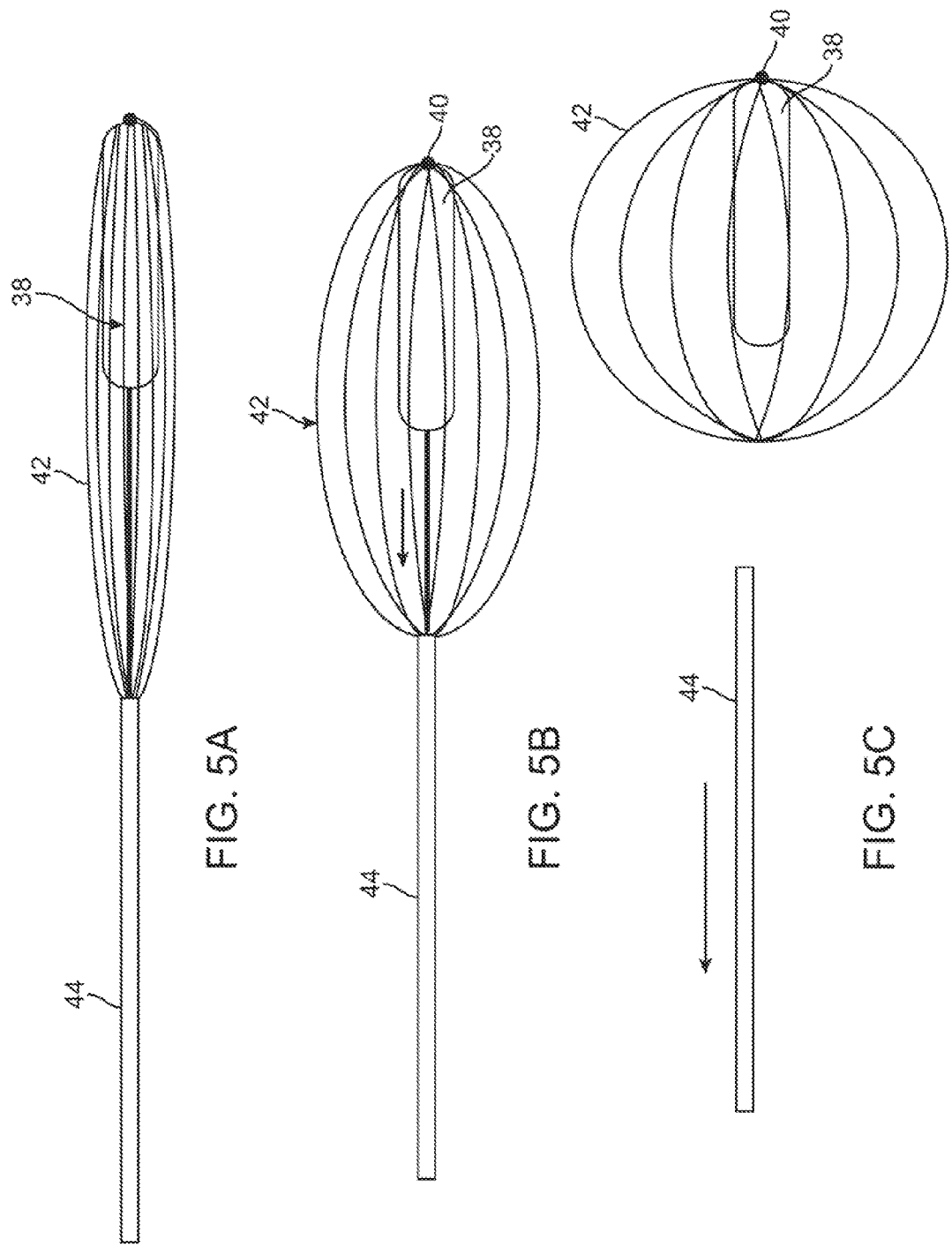

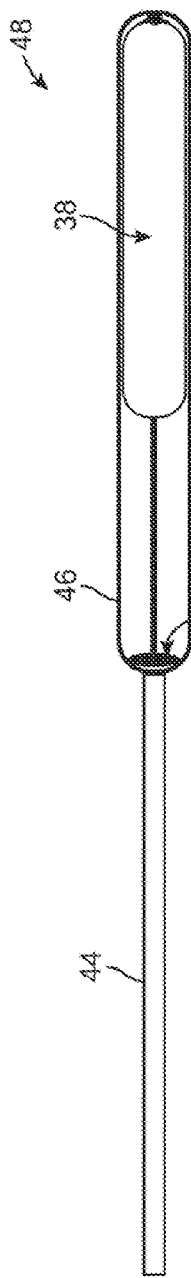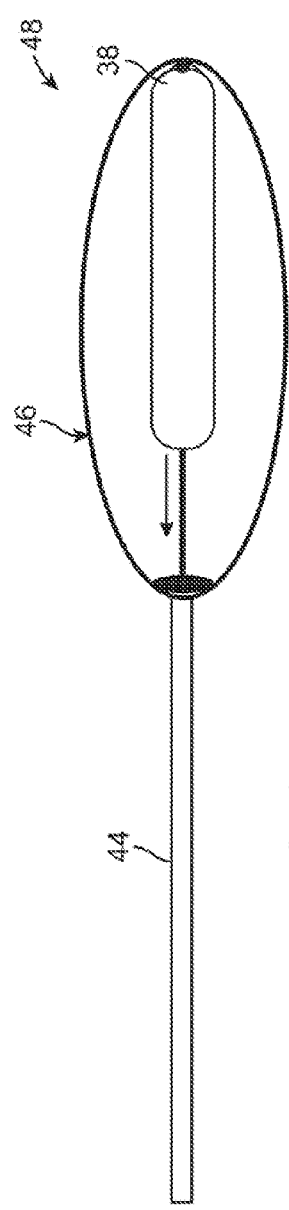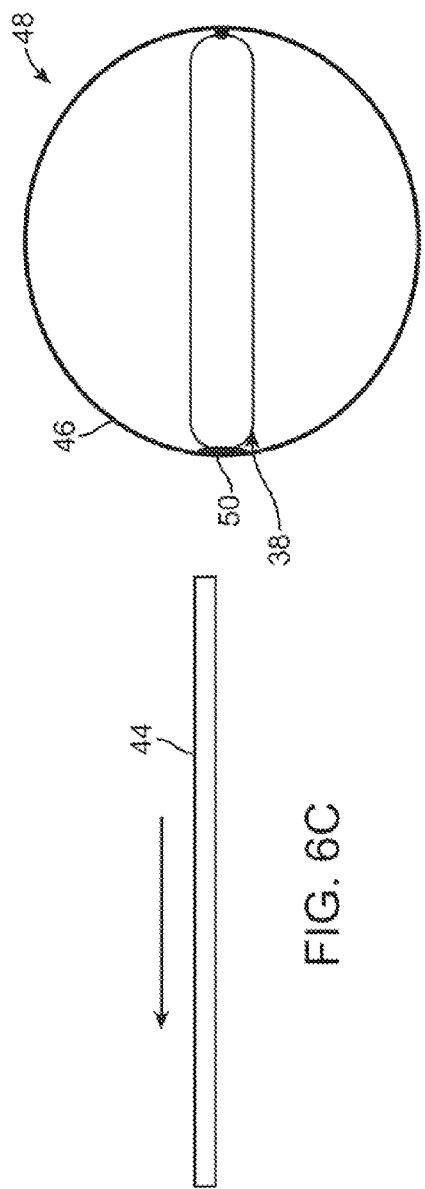

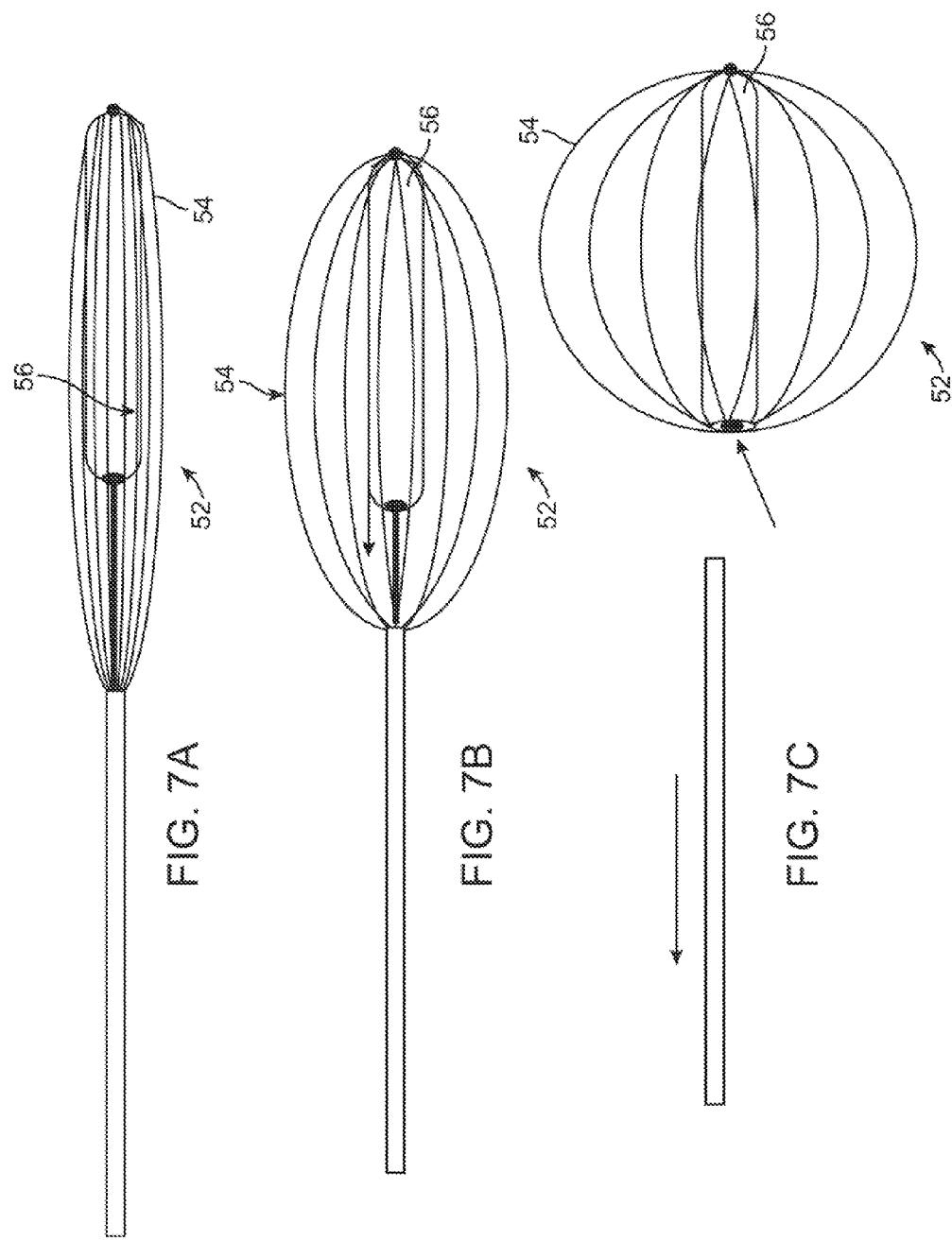

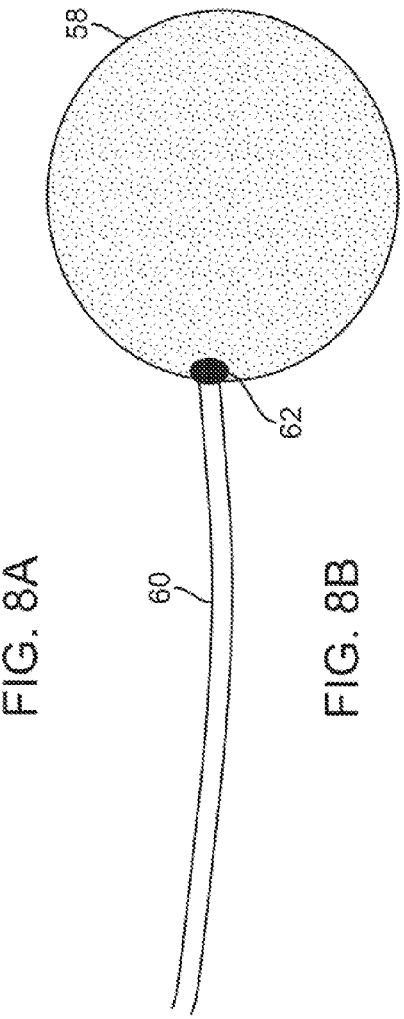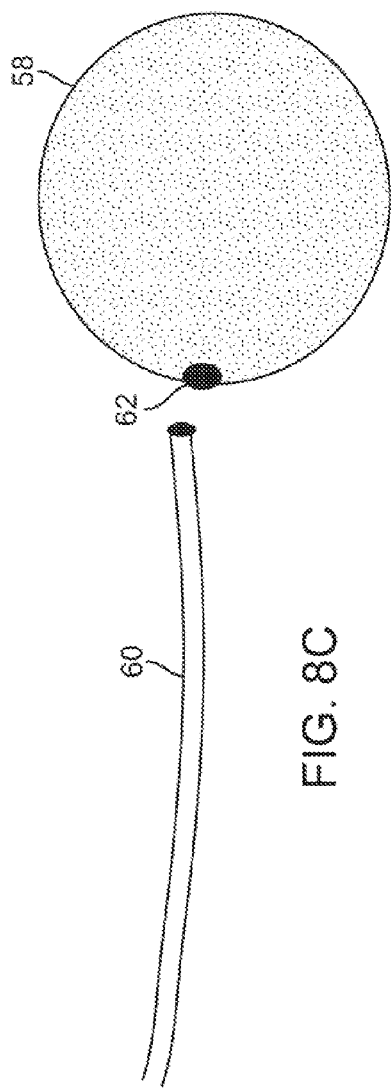

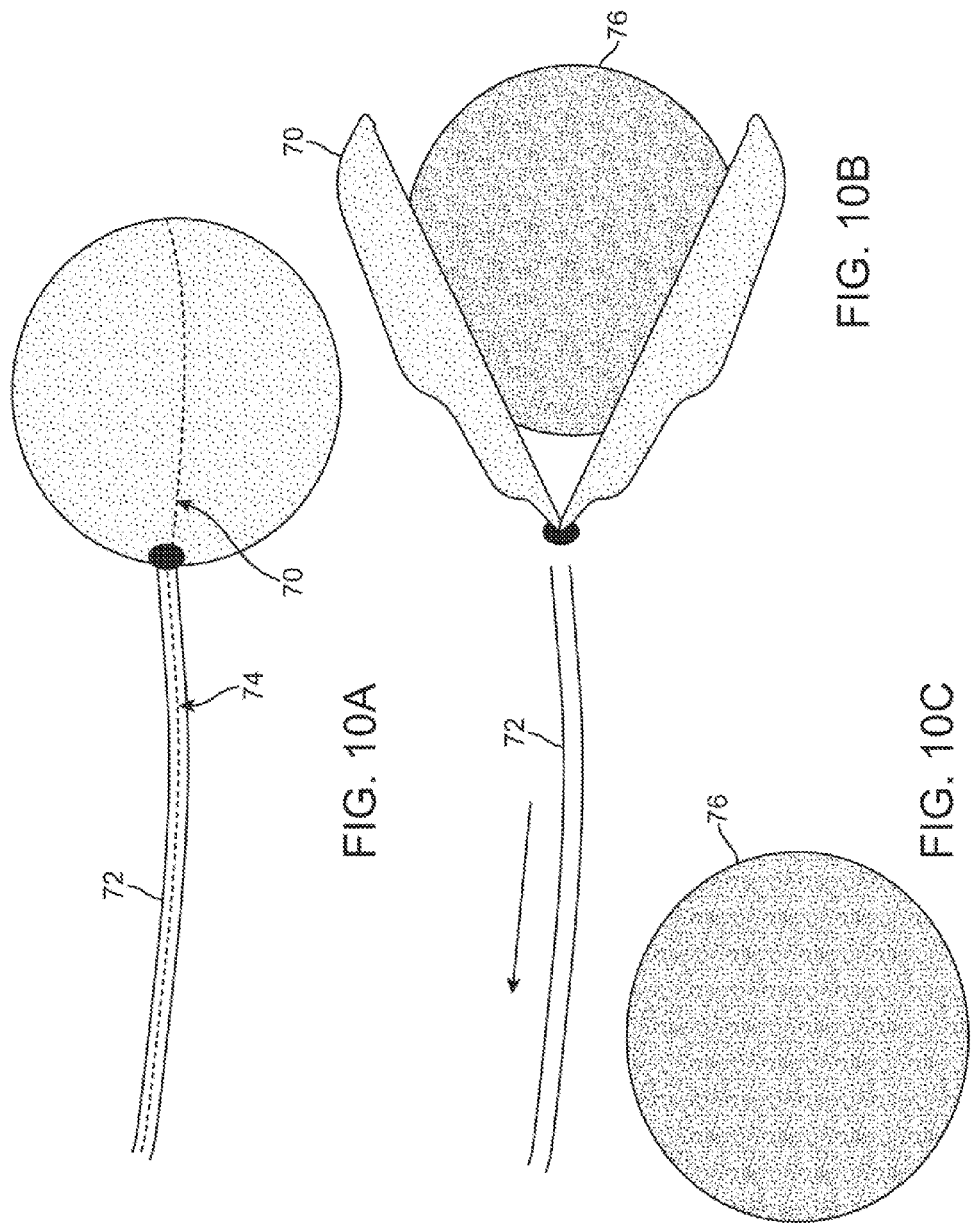

GASTRO-INTESTINAL DEVICE AND METHOD FOR TREATING ADDICTION

CROSS-REFERENCES TO RELATED APPLICATIONS

This application is a continuation-in-part of U.S. patent application Ser. No. 10/915,716 filed Aug. 9, 2004, currently pending, which is a continuation-in-part of U.S. patent application Ser. No. 10/833,950, filed Apr. 27, 2004, currently pending, which claims priority to U.S. Provisional Patent Application Ser. No. 60/525,105, filed Nov. 26, 2003 and which is a continuation-in-part of U.S. patent application Ser. No. 10/671,191, filed Sep. 24, 2003, which claims priority to U.S. Provisional Patent Application Ser. No. 60/490,421, filed Jul. 28, 2003, the disclosures of which are incorporated in their entirety by reference herein.

This application also claims priority to U.S. Provisional Patent Application Ser. No. 60/764,673 filed Feb. 3, 2006, the disclosure of which is incorporated in its entirety by reference herein.

BACKGROUND OF THE INVENTION

1. Field of the Invention

The present invention concerns a gastro-intestinal device for treating addiction and other medical conditions. More particularly, the present invention concerns a device that is positioned orally, nasally, or transcutaneously in a patient's gastro-intestinal tract and that, in some embodiments, delivers medications and/or noxious stimuli over extended periods of time.

2. Description of the Related Art

Alcoholism is an addictive condition that results in severe debilitation and that destroys the lives of millions of people every year.

Therapies known in the prior art for treating alcoholism involve counseling and enrollment in support groups, but counseling-based therapies have proven to be largely ineffective, as shown by the rate of recidivism for patients that have undergone such therapies.

Pharmacological therapies have also been attempted, which involve the prescription of one or more medications that the patient must ingest form time to time. One pharmacological therapy involves the prescription of antieuphorics, such as naltrexone, which reduce the euphoria induced by alcohol and which also reduce cravings during the withdrawal phase. Another pharmacological therapy involves the prescription of antitolerance agents, such as antabuse agents or tetraethylthiuram disulfide (known in the medical trade as disulfuram), which cause a range of unpleasant symptoms upon the ingestion of alcohol. These pharmacological agents may be effective if taken as prescribed but turn out to be ineffective in the majority of cases because their intake is typically not controlled and patients are free to forego their ingestion and return to their destructive behavior. Moreover, each of these medications may cause undesirable collateral effects.

In addition to alcoholism, dependency from many other harmful substances has been treated with therapies that have proven to be either ineffective or of limited duration. In addition to substance abuse, food abuse and obesity has been identified as major health problems that lead to a variety of illnesses and that decrease self-esteem, but treatments proposed to date typically provide only temporary benefits, because the patient can decide when to discontinue the treatment, or is unable to self-discipline herself to undergo the rigorous regimen required to overcome her condition. In order to reduce weight, patients sometimes resort to surgical procedures that are not only risky and expensive, but that sometimes require a long recuperative process.

Therefore, there is a need for a therapy that effectively treats substance addiction and abuse and that is not prone to altering or tampering by the patient.

Further, there is a need for a therapy that effectively treats substance addiction and abuse, and that either reduces the euphoria associated with substance abuse or that causes an adverse reaction discouraging the addictive behavior.

Still further, there is a need for a therapy that effectively treats substance addiction and abuse and that may be reversible, transient in nature, and implemented with non-invasive or minimally invasive procedures.

BRIEF SUMMARY OF THE INVENTION

The present invention concerns a device that can be positioned in a patient's gastro-intestinal tract and that, in certain embodiments, delivers oral medications and/or noxious stimuli over an extended period of time. The device of the present invention can be inserted and removed orally, nasally or transcutaneously and, in certain embodiments, expands reversibly once in the gastro-intestinal space.

In one embodiment, the device of the present invention is configured for treating alcoholism by delivering an anti-alcoholic agent at a predetermined rate and in a format that prevents patient tampering while providing the required daily amount of the agent. This embodiment may deliver any medicine absorbable across the gastro-intestinal tract and may include a retaining structure that is lockable and/or made of shape-memory materials, so to maintain the device in the desired configuration and condition, and confined within the gastro-intestinal space.

In this embodiment of the invention, the device is inserted orogastrically and expanded in the gastric space. The retaining structure is made of or coated with a biocompatible material that resists the harsh gastric environment; for example, the retaining structure may be manufactured from a silicone coated shape memory wire, or from a biocompatible metals rubber, polymer, etc. Further, the retaining structure may have a spherical shape, or any other shape that can be manufactured other shape produced from a polymer infused into a collapsible, preformed casing inside the gastric space. Such a casing will degrade over time exposing the polymer or may be extracted from the gastro-intestinal tract. Because the polymer is infused with a drug or other curative substance, the polymer structure will elute the drug or the curative substance over time into the intestine of the patient.

In certain embodiments of the invention, a dispensing member is positioned inside the device and includes a pump or other device suitable for delivering or eluting a drug into the gastro-intestinal tract. In another embodiments, the device includes one or more sensors coupled to a generator of noxious stimuli, so that, once the sensors detects one or more predetermined addictive substances, a noxious stimulus is generated, causing a negative feedback signal that becomes associated with the addictive substance. The noxious stimulus may be a vibratory sensation or an audible noise, or may trigger the release of a quick-acting, nausea-generating substance or the generation of uncomfortable electrical impulses into the stomach or the intestine. In still other embodiments, the device may be positioned transpylorically and includes a central portion spanning across the duodenal orifice and connecting two end portions disposed on opposing sides of the duodenal orifice.

In yet other embodiments, the retaining structure may include no dispensing member and may be employed for treating obesity by providing a sense of fullness in the stomach and by reducing appetite accordingly.

Methods of use of the present device for the treatment of alcoholism and other medical conditions are also described herein.

BRIEF DESCRIPTION OF THE SEVERAL VIEWS OF THE DRAWINGS

The drawings constitute a part of this specification and illustrate exemplary embodiments of the invention, which may be embodied in various forms. It is to be understood that in some instances various aspects of the invention may be shown exaggerated or enlarged to facilitate an understanding of the invention.

FIGS. 1A-1C illustrate side views of a first embodiment of the invention that includes a foldable reversible member.

FIGS. 2A-2B illustrate top views of the embodiment of FIGS. 1A-1C, showing the reversible member in the elongated and contracted configurations.

FIGS. 3A-3C illustrate top views of the embodiment of FIGS. 1A-1C, in which the reversible member transitions form the contracted configuration to the elongated configuration.

FIGS. 4A-4B illustrate top views of the embodiment of FIGS. 1A-1C, showing the reversible member coupled with the dispensing member.

FIGS. 5A-5C illustrate side views of a second embodiment of the invention, in which the reversible member is a wire cage containing the dispensing member.

FIGS. 6A-6C illustrate side views of a third embodiment of the invention, in which the reversible member is a locking sphere containing the dispensing member.

FIGS. 7A-7C illustrate side views of a variant of the embodiment of FIGS. 5A-5C, in which the reversible member is a lockable wire cage containing the dispensing member.

FIGS. 8A-8C illustrate side views of a fourth embodiment of the invention that includes a polymeric material injected into a casing.

FIGS. 10A-10C illustrate side views of a sixth embodiment of the invention that includes a polymeric material expanded within a casing that is later withdrawn from the patient.

DETAILED DESCRIPTION OF EMBODIMENTS OF THE INVENTION

Figure 9A:
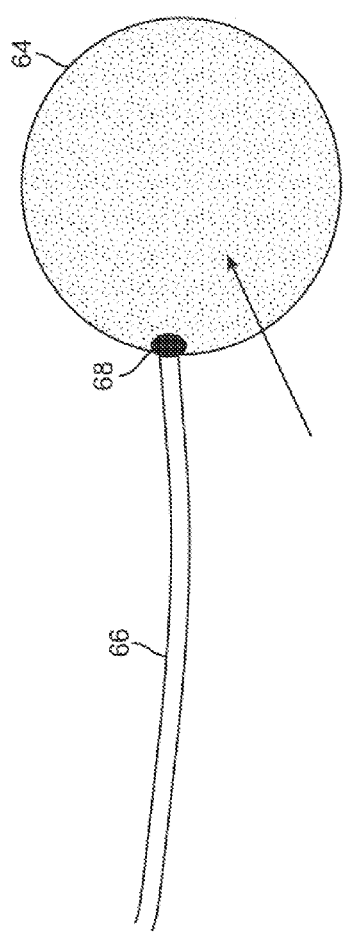
FIGS. 9A-9B illustrate side views of a fifth embodiment of the invention that includes a polymeric material disposed within a casing and expanded and hardened by the addition of a liquid material.

Detailed descriptions of embodiments of the invention are provided herein. It is to be understood, however, that the present invention may be embodied in various forms. Therefore, the specific details disclosed herein are not to be interpreted as limiting, but rather as a representative basis for teaching one skilled in the art how to employ the present invention in virtually any detailed system, structure, or manner.

Referring first to FIGS. 1A-1C, there is shown a first embodiment of the invention. Intragastric device 18 includes reversible member 20 that can be positioned in a patient's stomach or in other parts of the gastro-intestinal tract and that can assume an extended configuration before introduction in the stomach, as shown in FIG. 1A. Reversible member 20 can then be refolded after positioning in the stomach, as shown in FIGS. 1B and 1C.

Locking button 22 is connected to a tether and is used to force reversible member 20 to fold on itself and to maintain the folded configuration. More particularly, locking button 22 is progressively pulled through locking lumen 24 by pulling on both ends of string 26, causing locking button 22 to traverse locking lumen 24 while reversible member 20 progressively assumes a contracted, essentially spherical configuration. After locking button 22 has completely traversed locking lumen 24 and reversible member 20 is securely formed in the contracted configuration, string 26 can be removed by pulling on one end of it and by having string 26 rotate around and release from locking button 22. Alternatively, string 26 may be removed by cutting it in the proximity of locking button 22 with the use of endoscopic tools, or with the use of other medical or surgical techniques known in the art.

Intragastric device 18 may be inserted in a patient's stomach or in other parts of the gastro-intestinal tract to provide a variety of gastric-related benefits, including the reduction and eradication of an addiction by providing, for example, gastric stimulation, drug release, or noxious stimuli. Additionally, intragastric device 18 may be used with or without a pylorus-spanning element and a duodenal bulb extending from reversible member 20, as described in greater detail below. The specific embodiment of intragastric device 18 illustrated in FIGS. 1A-1C does not include a pylorus-spanning element.

Referring now to FIGS. 2A-2B and 3A-3C, one example of the removal features of intragastric device 18 is described. Retrieval tether 28 is connected to retrieval ball 30 and is cast loosely in the periphery of reversible member 20, and more firmly in the central portion of reversible member 20. Retrieval ball 30 may be the same as locking button 22 or may be a separate component of intragastric device 20. Anchor 32 may also be provided, to prevent an undesired tearing of intragastric device 20 when tension is applied to retrieval ball 30.

In the illustrated example, intragastric device 18 may be removed by snaring retrieval ball 30 (attached to retrieval tether 28) with snare 34, causing retrieval tether 28 to open rip-strip 36 and further causing reversible member 20 to assume an unfolded configuration suited for removal through the esophagus. Conversely, this and other embodiments of intragastric device 18 may include a locking feature that will prevent the unfolding of reversible member 20 in the gastric space and that will require endoscopic manipulation for removal, in order to unlock reversible member 20 and for extracting it through the esophagus or through surgery.

Referring now to FIGS. 4A-4B, intragastric device 18 also includes dispensing member 38, which is disposed within reversible member 20 and which can provide a drug or a stimulus (for example, a vibratory, acoustic stimulus, or electric stimulus) to the patient's stomach or gastro-intestinal tract. One skilled in the art will appreciate that other types of stimuli may also be provided, which are all included within the scope of the present invention.

A plurality of ancillary components, such as sensors and actuators, also may be included in intragastric device 18. For example, sensors may be included that are capable of sensing virtually any substance, including substances of addiction. Actuators also may be included, such as drug pumps or other release devices that provide a constant or sensor-triggered elution of a drug and/or noxious stimulus, for example, a vibratory, auditory, or electrical shock signal, or the release a short-acting noxious compound. Intragastric device 18 may also incorporate refilling/recharging port 40, designed to engage endoscopic tools and/or a specially designed catheter. Such a catheter may be magnetically tipped and may engage intragastric device 18 in a variety of ways, one of which is illustrated in FIGS. 16A-16D, discussed in greater detail below. In addition, intragastric device 18 may be recharged, programmed or interrogated either through the catheter mechanism or with an external signal/power generator and/or receiver, connected transcutaneously or wirelessly to intragastric device 18. Communication devices, data receivers, data storage modules, microprocessors and rechargeable power sources also may be included in intragastric device 18.

Referring now to FIGS. 5A-5C, there is shown a second embodiment of the invention, in which the reversible member is a shape-memory scaffold or cage 42 that is shaped to maintain the gastric position of dispensing member 38. This embodiment may incorporate all of the features of the previously mentioned embodiment and can be inserted and extracted through an expansion and compression process of cage 42.

Cage 42 is made from or coated with a biocompatible material and expands after positioning in the stomach. More particularly, cage 42 is compressed to an elongated configuration prior to insertion in the stomach and is then disposed in the stomach with the help of positioning catheter 44. After the positioning of cage 22 is completed, catheter 44 is detached from cage 42 and withdrawn from the gastro-intestinal tract. In this embodiment, dispensing member 38 remains connected to one end of cage 42, eluting a drug or a stimulus through port 40.

Turning now to FIGS. 6A-6C, there is shown a third embodiment of the invention. Intragastric device 48 includes a shape-memory and/or locking cage 46 that operates as a scaffold to maintain the gastric position of dispensing member 38. Intragastric device 48 can be inserted into and extracted from the gastro-intestinal tract by expanding and compressing age 46 and/or by locking and unlocking cage 46, to maintain the contracted configuration and to ensure that intragastric device 48 will not migrate away from the stomach and into the gastro-intestinal tract and also to ensure that dispensing member 38 does not migrate from the gastric space. Locking port 50 may be manipulated using standard endoscope tools in order to facilitate insertion and/or extraction of intragastric device 48, and, once locking is achieved, dispensing member 38 will span across diametrally opposite points on the surface of reversible member 46, with one end of dispensing member 38 reversibly engaging port 50. Cage 46 may have a continuous surface, or a surface defined by a plurality of struts with openings therebetween. Intragastric device 48 may incorporate some or all of the features of the previously described embodiments and may include a sensor, an actuator, a recharging/refilling port, an external communicator, and similar components.

Turning now to FIGS. 7A-7C, there is shown another embodiment 52 of the invention, in which reversible member 54 is structured like a shape-memory and/or locking scaffold 54 and is used to maintain the gastric position of intragastric device 52. In this embodiment, locking scaffold 54 is non-continuous, allowing gastric juices to flow in and around dispensing member 56.

FIGS. 8-11 illustrate other embodiments of the invention, in which the drug to be eluted is encapsulated in a polymer that expands after injection into a mold in the stomach. These embodiments allow for polymeric mass to acquire and initially retain a large volume inside the gastro-intestinal tract while having a very low insertion profile. In each of these embodiments, a casing, or mold, is used to shape the polymer or the polymer is simply injected into the casing with a catheter, or is provided or injected in the casing in a dehydrated state and is then rehydrated. The casing may be produced from a flexible or a rigid material.

More particularly, in the embodiment illustrated in FIGS. 8A-8C, a polymer is injected into casing 58 through catheter 60, which is engaged in fluid communication with casing 58 at injection port 62. The injection of the polymer causes casing 58 to swell and acquire a predetermined shape (spherical in the illustrated embodiment), after which catheter 60 is detached from injection port 62 while the polymer solidifies within casing 58. Casing 58 is manufactured from a biodegradable product, which dissolves into the gastro-intestinal tract over time, leaving the polymer exposed to gastro-intestinal fluids. The polymer itself may or may not be soluble in the gastro-intestinal tract, that is, may retain its shape over time or progressively dissolve.

Figure 9B:
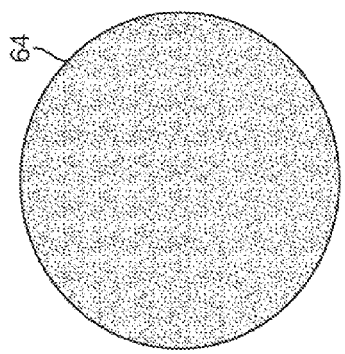

In the embodiment illustrated in FIGS. 9A-9B, a polymer is disposed or injected within casing 64 is in a dry state, and a liquid (for example, a saline solution) is then injected into casing 64 through catheter 66 and injection port 68. The addition of the liquid causes the polymer to swell and harden. Also in this case, the casing is manufactured from a biodegradable material, which dissolves in the gastro-intestinal tract over time. The polymer itself is also manufactured from a biodegradable material and may or may not dissolve over time.

In the embodiment of FIGS. 10A-10C, casing 70 is shaped like a clamshell, into which the polymer is injected through catheter 72. Rip-strip 74 is connected to casing 70, allowing clamshell 70 to open along a rip-strip line on casing 70 while still maintaining contact between catheter 72 and casing 70 after expansion of the polymer, so to enable removal of casing 70 through the mouth or nose of the patient. Hardened polymer body 76 is then released in the stomach or other part of the gastro-intestinal tract, as determined appropriate by the clinician. As in previous embodiments, polymer body 76 may or may not dissolve within the gastro-intestinal tract over time.

Figure 11A:
FIGS. 11A-11C illustrate perspective views of the embodiment of FIGS. 8A-8C, in which the polymer is shaped into a toroidal structure.
Figure 11B:
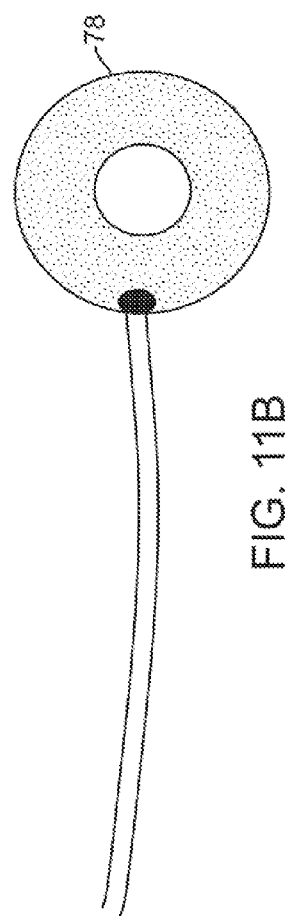
Figure 11C:
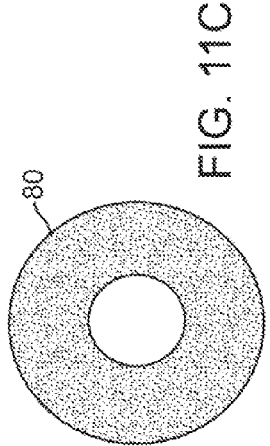

The previously described embodiments have been illustrated with reference to a hardened polymer that assumes an essentially spherical shape. One skilled in the art will appreciate that a plurality of other configurations are possible. For example, the polymer may be injected or expanded into toroidal casing 78 and then harden to assume toroidal configuration 80, as shown in FIGS. 11A-11C. A plurality of other configurations are also possible and within the scope of the present invention.

In any of the embodiments of FIGS. 8-11, the polymer may be infused with a drug, which is slowly released or may be used as an anchor for a dispensing member that provides noxious stimuli within the gastric space. The above-described embodiments may also be used for the treatment of obesity, due to their gastric space-occupying nature. By use of the above described embodiments, a durable effect is achieved that may vary over time, and such devices may be placed into the gastro-intestinal tract via the nasogastric or orogastric route with little to no anesthesia.

Figure 12:
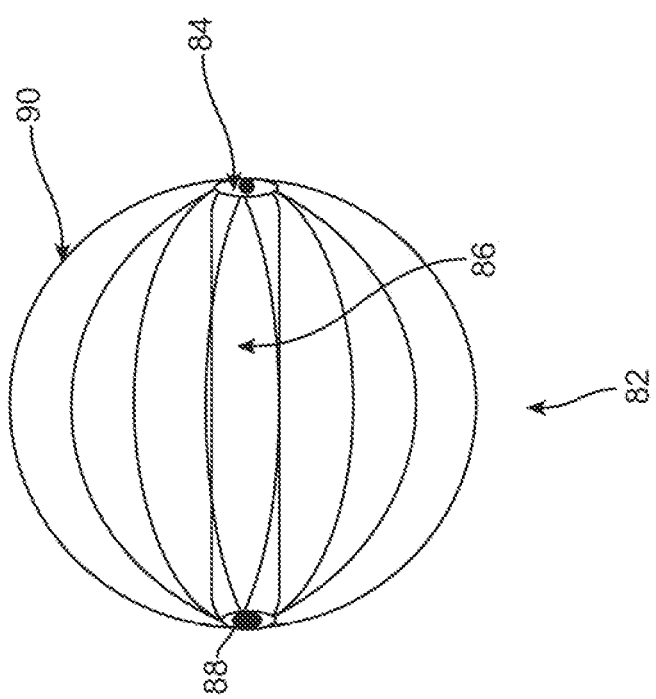
FIG. 12 illustrates a perspective view of the device of FIG. 7C, in which the dispensing member provides noxious stimuli

FIG. 12 illustrates the intragastric device of FIGS. 7A-7C, to which a sensor and actuator may be added. In intragastric device 82 and in other embodiments of the invention, the sensor may be designed to sense virtually any substance, including substances of addiction. For example, gastric sensor 84 may be an alcohol sensor. The actuator in intragastric device 82 and in other embodiments may be a drug pump that is disposed within dispensing member 86 and that provides constant or sensor-triggered elution of a drug and/or the generation of a noxious stimulus, for example, a vibratory, auditory, or electrical shock signal, the release of a short-acting noxious compound, etc. Intragastric device 82 may also incorporate refilling/recharging port 88, which is designed to engage endoscopic tools or a specially designed catheter, for example, a magnetically-tipped catheter that is designed to engage a complementary region of the device, as illustrated in FIGS. 16A-16D. Intragastric device 82, and other embodiment of the invention, may also be recharged, programmed or interrogated either through the catheter mechanism or via an external signal and power generator/receiver. Any data provided to or generated by intragastric device 82 may be processed and stored in appropriate equipment also disposed within intragastric device 82. Further, in this and in other embodiments, struts 90 can not only provide a structural function and a support function for dispensing member 86, but can also act as electrodes to pace and shock the stomach.

Figure 13A:
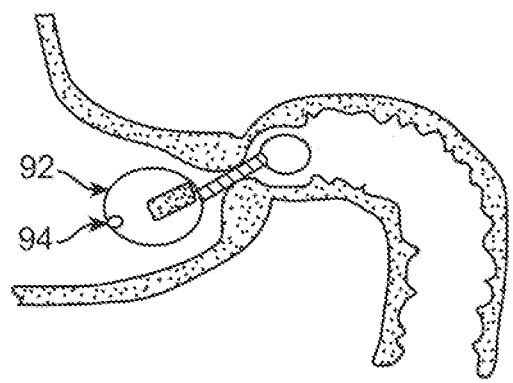
FIGS. 13A-13C are schematic illustrations of an embodiment of the invention that provides energy stimulation to the pylorus.
Figure 13B:
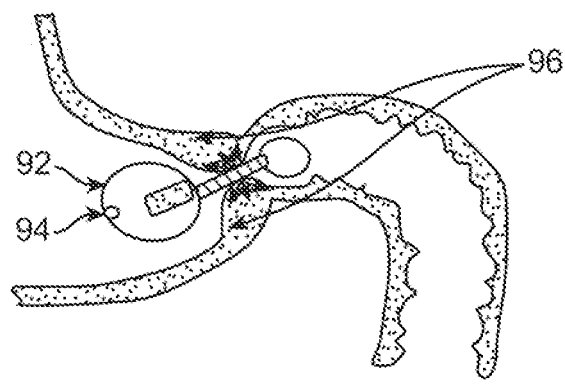
Figure 13C:
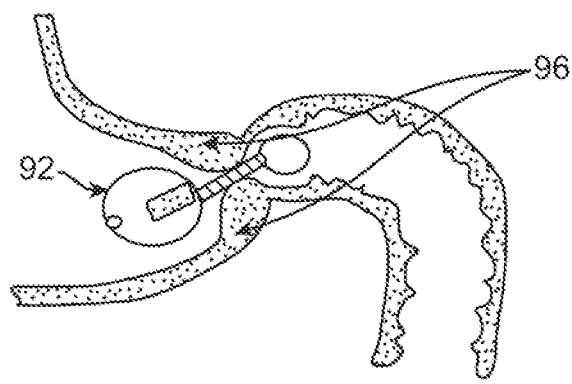

Turning now to FIGS. 13A-13C, there is shown an embodiment of the invention that stimulates the gastro-intestinal tract with electrical, acoustic or vibratory signals. When device 92 is disposed in the trans-pyloric position as shown, device 92 can sense substances in gastric and/or intestinal spaces and can then transmit noxious stimuli (for example, acoustic, vibratory, and electrical signals) to the gastric or intestinal space. As shown in FIG. 13A, a drug or addictive substance may be detected with sensor 94, and, as further shown in FIG. 13B, energy would then be transmitted to the pylorus, stomach or intestine in response to the detected substance (in FIG. 13B, energy is depicted as being transmitted to pylorus 96). The transmission of energy or noxious stimuli may continue for a fixed period of time only after the substance is sensed or may cease once the substance has been cleared and is no longer sensed by the device, as shown in FIG. 13C, in which no energy is being depicted as transmitted to pylorus 96.

Figure 14A:
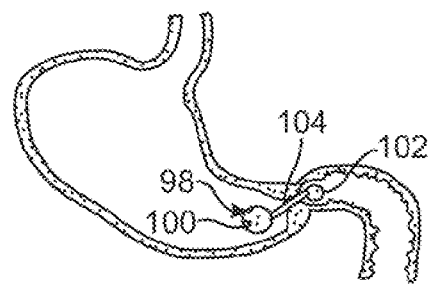
FIGS. 14A-14D are schematic illustrations of an embodiment of the invention that includes a contracting pylorus spanning element.
Figure 14B:
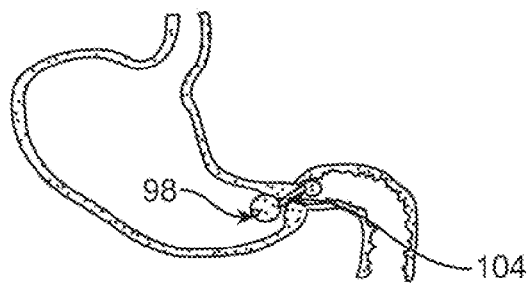
Figure 14C:
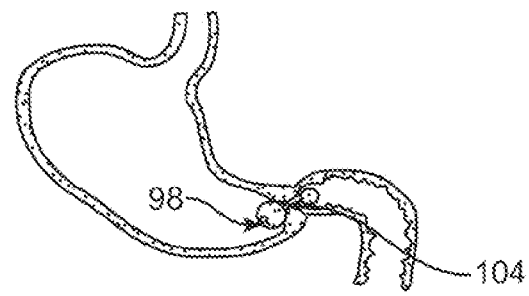
Figure 14D:
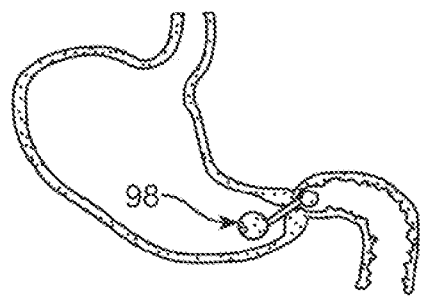

FIGS. 14A-14D illustrate still another embodiment of the invention, which is structured for obstructing the gastric outlet. As shown in FIG. 14A, device 98 includes a proximal member 100, positioned on the stomach side of the gastric outlet, and a distal member 102, positioned on the opposite side of the gastric outlet. Proximal member 100 and distal member 102 are connected by pylorus spanning member 104. When device 98 is not sensing the offending (addictive) substance, pylorus spanning member 104 is in an elongated configuration, providing little to no obstruction of the gastric outlet. Once the offending substance is sensed, pylorus spanning member 104 contracts, effectively greater reducing, or temporarily eliminating, gastric outflow, as shown in FIGS. 14B and 14C. The contraction of the pylorus spanning member 104 will cause the patient to feel full much more quickly and to ingest less of the addictive substance, for example, less alcohol. A full outlet obstruction is also likely to cause nausea and dyspepsia, which the patient will associate with the addictive substance, forming an aversion to said addictive substance. When no addictive substance is sensed any longer, pylorus spanning member 104 extends again to its initial length, as shown in FIG. 14D, relieving the obstruction of the gastric outlet and also relieving dyspepsia.

Figure 15A:
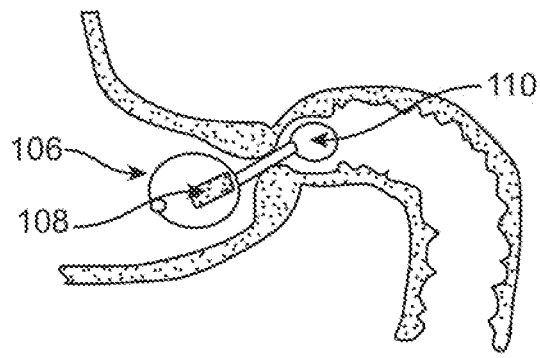
FIGS. 15A-15C are schematic illustrations of an embodiment of the invention that includes a pylorus spanning element and one or more electrodes disposed on opposing sides of the duodenal orifice.
Figure 15B:
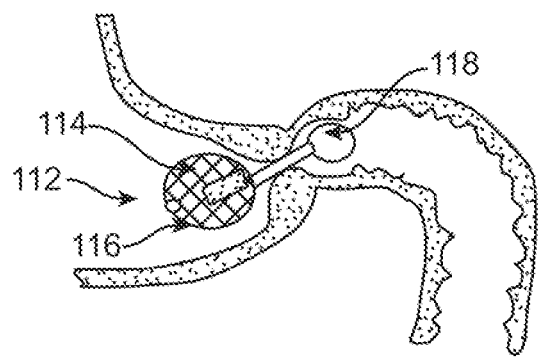
Figure 15C:
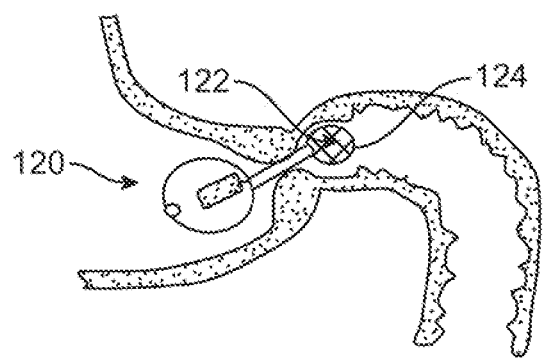

FIGS. 15A-15D illustrate alternative embodiments of the invention that cause noxious stimuli to the patient. In FIG. 15A, there is shown gastric device 106 that includes vibratory or acoustic element 198, and that also an optional tether and distal bulb 110. In FIG. 15B, there is shown gastric device 112 that includes electrode 114 disposed on proximal element 116. Even in gastric device 112, an optional tether and distal bulb 118 are included. In FIG. 15C, there is shown gastric device 120, which includes distal element 124 disposed in the duodenum and which includes electrode 122 disposed on distal element 124. One skilled in the art will recognize that these are but some examples of possible embodiments and should not be taken as limiting the scope of the invention. For example, a device according to the principles of the present invention may include a plurality of generators of noxious stimuli coupled with one or more sensors disposed in a gastrically retained, intestinally retained or gastro-intestinally retained device.

Figure 16A:
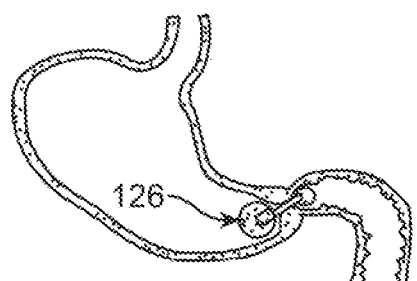
FIGS. 16A-16D are schematic illustrations of the charging, refilling or programming of a transpyloric embodiment of the invention that is attached to a catheter.
Figure 16B:
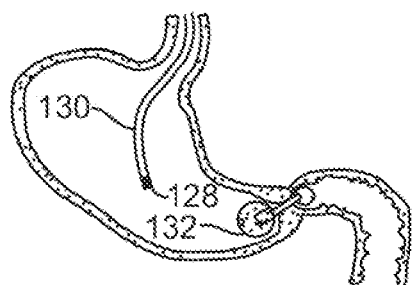
Figure 16C:
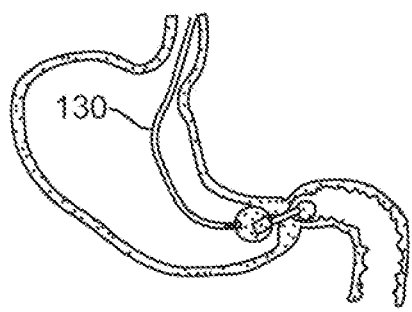
Figure 16D:
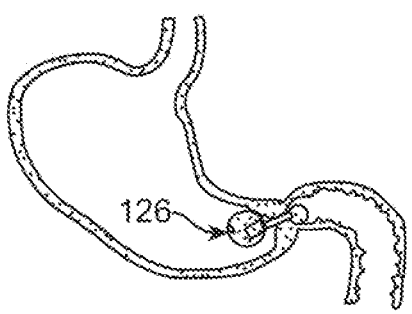

FIGS. 16A-16D illustrate the charging, refilling or programming of a gastric device constructed according to the principles of the present invention. Device 126 is initially disposed in transpyloric position, as shown in FIG. 16A, but the same device and method for charging, refilling or programming applies likewise to a fully intragastric device or even to a fully intestinal device. Charger, refiner or programmer 128 is attached to catheter 130, as shown in FIG. 16B, and may be inserted orally or nasally into the gastric space with or without the help of imaging capabilities. When imaging capabilities are employed, catheter 130 is directed towards charging, refilling or programming port 132, and gastric device 126 is engaged and altered, as shown in FIG. 16C. The catheter is eventually extracted, leaving device 126 in place, as shown in FIG. 16D. Alternatively, a magnetically tipped catheter could be used to engage a conducting metal ring at the site of manipulation, and the catheter may be inserted blindly and register (for example, through a noise, a light, etc.) once the catheter has engaged the device. The gastric device may then be charged, refilled, programmed or even removed once it has been engaged.

Any suitable materials may be used to produce the embodiments of the invention described herein. In one type of embodiment, for example, a gastric device may comprise an expandable balloon or casing fabricated from silicone, silicone elastomers, latex, polyurethane, PTFE, FEP, and/or the like. Likewise, self-expanding materials, such as foam or hydrogels that typically expand upon contact with fluids, may be utilized as polymers within the device.

In all gastric embodiments, the proximal portion of the gastric device has a supportive or structural function and a large enough cross sectional diameter that prevents passage of the device through the pyloric valve. The distal portion of the gastric device typically contacts the pyloric valve and/or tissue adjacent the pyloric valve, intermittently and/or partially blocking the valve or providing electrical stimulation.

In some embodiments, the distal portion of the gastric device is made of a compliant material, so that it does not harm the tissue when it contacts stomach tissue in, around or adjacent the pyloric valve. Also in some embodiments, the proximal and distal portions are produced from the same material, with the proximal portion having a greater amount of material, greater wall thickness or similar structural features relative to the distal portion. Alternatively, any of the above-described embodiments could be altered to allow for anchoring in the duodenal bulb. As with the pyloric sphincter in the stomach, the duodenal bulb necks down to a smaller lumen, creating an effective sphincter.

Any of the previously described embodiments can be configured to provide for retention in the duodenal bulb without an excessively firm stenting or without puncturing the intestinal wall. In fact, any of the previously described embodiments can be endoscopically delivered and removed, and can be retained within the stomach and/or the duodenum without attachment to the wall of the gastro-intestinal tract. Therefore, the present invention enables an effective stimulation of the intestine without the need for a gastric component.

Likewise, an embodiment of the present invention could be used to anchor a gastrointestinal energy delivery device in any region of the gastro-intestinal tract where there is a decrease in the diameter of the lumen that is sufficient to maintain an interference fit. This includes the pharynx, the esophagus (upper, cardiac and lower sphincters), the pylorus, the duodenal bulb, the ileocecal valve, the rectum and any other region with a change in diameter sufficient for anchoring a stimulating device through an interference fit.

As previously discussed, a gastric device according to the present invention may be covered by an erodable or biodegradable covering for delivery into the stomach. Such a covering may be configured to constrain the device, and may naturally break down and dissolve after the covering comes into contact with substances in the gastric lumen, thus releasing the device and allowing it to expand. In one embodiment, a gastric device according to the present invention may be covered by different materials each configured to erode at differing rates or in different chemical environments within the stomach.

Also as previously discussed, any of the embodiments described hereinbefore and illustrated in FIGS. 1-16 may include one or more dispensing members that generate noxious stimuli, one or more sensors, or a combination of both. Such dispensing members and sensors may be coupled with any portion of an anchoring device, pyloric corking device or the like, for example, any portions of the gastric device that reside in the stomach, span the pyloric valve or are disposed within the duodenum. In some embodiments, one or more dispensing members or sensors are coupled with an anchoring device or corking device via one or more tethers, while in other embodiments all the dispensing members and/or sensors may be coupled directly to the anchoring member.

Among the actuators that may be coupled with an anchoring device is an energy transmitter that applies energy to gastrointestinal tissue, for example, one or more of radiofrequency, ultrasound, microwave, cryogenic, laser, electrical, mechanical and thermal energy. One or more substances, such as lipids, drugs, enzymes, diagnostic agents, vitamins, minerals, and the like, also may be releasably coupled with the outer surface of the device or may be housed within one or more refillable reservoirs. These substances may be detachably coupled to the anchoring device or may be disposed within the reversible member.

Still another type of actuator is a member for occupying space in the patient's stomach, so to enhance the patient's feeling of satiety. Yet another type of actuator is a trigger adapted to elicit a biological response, such as a surface coating adapted to induce a satiety response. One more type of actuator is an imaging device, but, more generally, any component suitable for performing a function within the gastrointestinal system may be coupled to an anchoring device and to a pyloric corking device, or may be disposed within the reversible member.

In some embodiments, at least one sensor may be coupled to the anchoring member for sensing one or more characteristics of the gastrointestinal tract, for example, pH, temperature, bile content, nutrient content, fats, sugars, alcohol, opiates, drugs, analytes, electrolytes, or hemoglobin. Further, a processor may be included that is adapted to process data related to the sensed signals and to provide the processed data and other signals to the at least one energy delivery member. Still further, a receiver may be included that receives data transmitted from a remote source, or a transmitter for transmitting data, or a data storage module, or a rechargeable power source, or any suitable combination thereof.

As previously discussed, in some embodiments an anchoring device and/or a generator of noxious stimulus may be delivered by means of an elongate catheter device, such as an orogastric or nasogastric tube passed through the patient's esophagus and into the stomach. The catheter device or a separate device may be employed for modifying, adjusting or recharging an anchoring or dispensing device that has been positioned in the gastro-intestinal tract, thereby enabling a modification of the gastric device without removing or replacing the device.

Further, a gastric device according to the present invention may be used to detect ingestion of an addictive substance and records exposure to an undesired substance without delivering any noxious stimuli. This embodiment may be useful in screening patients for liver or other transplants where maintaining a non-addictive behavior is critical.

The present invention is particularly applicable to the treatment of a variety of addictive conditions, such as alcoholism, and to the treatment of obesity. By using a device constructed according to the principles of the present invention, a patient is left without discretion about undergoing the prescribed regimen, because the patient is unable to manipulate the device and to prevent it from operating as planned. At the same time, a clinician can adjust the device as necessary by using, for example, one the previously described adjustment methods. A device constructed according to the principles of the present invention also can be configured to be temporary, either by incorporating removal features, as previously described, or by being manufactured from one or more materials that dissolve over time within the body system.

While the invention has been described in connection with the above described embodiments, it is not intended to limit the scope of the invention to the particular forms set forth, but on the contrary, it is intended to cover such alternatives, modifications, and equivalents as may be included within the scope of the invention. For example, one skilled in the art will recognize that the devices and methods described herein may be used to treat a variety of other conditions or perform a variety of other function within the gastrointestinal tract and without departing from the scope of the present invention. Therefore, the foregoing description is provided primarily for exemplary purposes and should not be interpreted to limit the scope of the invention as it is defined in the following claims.

What is claimed is:

1. A device for treating obesity and/or addiction, the device comprising:
   a reversible member structured to have an elongated configuration during insertion into a patient's gastro-intestinal tract and a contracted configuration after the insertion;
   a locking button positioned along the reversible member;
   a length of string slidably attached to the locking button;

a dispensing member coupled to the reversible member,
wherein a distal end of the elongated configuration is coupled to a proximal end of the elongated configuration via the length attached to the locking button where the length is passed entirely through a locking lumen defined through the distal end such that the proximal end is approximated into and through the distal end until the locking button has traversed the locking lumen into the contracted configuration, and wherein the length is removable from the locking button by tensioning one end of the string once the reversible member is in the contracted configuration.

2. The device of claim 1, wherein the reversible member is positioned in the stomach or in the duodenal bulb.

3. The device of claim 1,
wherein the distal end is caused to roll and couple with the proximal end after the insertion to form the contracted configuration,
wherein the distal end is essentially spherical, and
wherein the distal end is releasable from the proximal end, providing for the reversible member to revert to the elongated configuration prior to removal from the patient's gastrointestinal tract.

4. The device of claim 1, wherein the dispensing member releases one or more of a drug and a stimulus into the patient's gastro-intestinal tract after the insertion.

5. The device of claim 4,
wherein the distal end is caused to roll and couple with the proximal end after the insertion to form the contracted configuration,
wherein the distal end is essentially spherical,
wherein the distal end is releasable from the proximal end, providing for the reversible member to revert to the elongated configuration prior to removal from the patient's gastro-intestinal tract, and
wherein the dispensing member is disposed adjacent to the proximal end in the elongated configuration, and wherein the dispensing member is connected to an opening in the contracted configuration.

6. The device of claim 4, wherein the reversible member is a cage containing the dispensing member, and wherein the cage has an essentially spherical configuration in the contracted configuration.

7. The device of claim 6, wherein the cage is produced from a shape memory material.

8. The device of claim 6, wherein the elongated configuration has a distal end and a proximal end, and wherein the dispensing member is connected to the proximal end.

9. The device of claim 6, wherein the dispensing member connects diametrally opposing ends in the essentially spherical configuration, and wherein the dispensing member is locked into position within the cage in the essentially spherical configuration.

10. The device of claim 6, wherein the cage has an essentially continuous outer surface.

11. The device of claim 6, wherein the cage has an outer surface formed by a plurality of struts.

12. The device of claim 4, wherein the dispensing member comprises a drug pump.

13. The device of claim 12, wherein the drug pump provides a constant or sensor-triggered elution of a drug.

14. The device of claim 4, wherein the dispensing member comprises a generator of a noxious stimulus.

15. The device of claim 14, wherein the noxious stimulus is a vibratory stimulus, an auditory stimulus, an electrical stimulus, or a short-acting noxious compound released into the patient's gastro-intestinal tract.

16. The device of claim 4, further comprising one or more of a sensor, an actuator, a communication device, a data storage module, a microprocessor, and a rechargeable power source.

17. The device of claim 4, wherein the dispensing member comprises one or more of a refilling port, a recharging port, and a programming port designed to engage a catheter or an endoscopic tool.

18. The device of claim 4, wherein the dispensing member is coupled to an electrode disposed in the gastro-intestinal tract.

19. The device of claim 4, wherein the reversible member is positioned in the stomach, and wherein the device further comprises a bulb positioned in the intestinal tract and connected to the reversible member by a pylorus spanning member.

20. The device of claim 19, wherein the dispensing member releases one or more of the drug and the stimulus by releasing the one or more of the drug and the stimulus through the pyloric spanning member.

21. The device of claim 19, wherein the pylorus spanning member contracts upon contact with a predetermined substance, thereby causing the bulb to block exit from the stomach into the intestinal tract.

22. The device of claim 1, wherein the reversible member is made of a compliant material.

* * * * *